United States Patent [19]

Ohnishi et al.

[11] Patent Number: 4,608,253

[45] Date of Patent: Aug. 26, 1986

[54] PROCESS FOR REMOVING IMMUNE COMPLEX IN BLOOD BY USE OF THE IMMOBILIZED PEPSIN

[75] Inventors: Haruo Ohnishi, Funabashi; Hiroshi Kosuzume, Yokohama; Yasuo Suzuki, Kawaguchi; Ei Mochida, Tokyo, all of Japan

[73] Assignee: Mochida Pharmaceutical Co., Ltd., Tokyo, Japan

[21] Appl. No.: 556,709

[22] PCT Filed: May 31, 1982

[86] PCT No.: PCT/JP82/00212

§ 371 Date: Nov. 15, 1983

§ 102(e) Date: Nov. 15, 1983

[87] PCT Pub. No.: WO83/04180

PCT Pub. Date: Dec. 8, 1983

[51] Int. Cl.$^4$ .............................................. A61K 37/54
[52] U.S. Cl. ....................................... 424/94; 435/269
[58] Field of Search ......................... 424/94; 604/4–6; 435/269

[56] References Cited

FOREIGN PATENT DOCUMENTS 51-38195  10/1976  Japan .
52-151723 12/1977  Japan .
56-72868   6/1981  Japan .
57-13266   3/1982  Japan .

OTHER PUBLICATIONS

The Journal of Clinical Investigation, vol. 57 (1976–1975), D. Terman et al. "Degradation of Circulating DNA", pp. 1201–1212.
Butler et al.–Chem. Abst., vol. 89 (1978) p. 105700w.
The Merck Index–9th edition (1976) p. 6942.

*Primary Examiner*—Sam Rosen
*Attorney, Agent, or Firm*—Parkhurst & Oliff

[57] ABSTRACT

The present invention relates to immobilized pepsin for use in removing immune complex which comprises pepsin fixed on a suitable carrier, and to a process for removing immune complex which comprises bringing blood or plasma from a patient suffering from an immune complex disease, such as rheumatoid arthritis and systemic erythematosus, into contact with the immobilized pepsin.

20 Claims, No Drawings

PROCESS FOR REMOVING IMMUNE COMPLEX IN BLOOD BY USE OF THE IMMOBILIZED PEPSIN

TECHNICAL FIELD

The present invention relates to immobilized pepsin for use in removing immune complex from blood and to a process for removing immune complex from blood by the use of the immobilized pepsin.

BACKGROUND ART

Auto immune disorders or immune complex diseases, typified by rheumatoid arthritis, systemic lupus erythematosis (SLE), and lupus nephritis, are, as the names imply, disorders caused by a complex of various antigens and antibodies, that is, an immune complex. The mechanisms of immune complex diseases are so complicated that many points still remain for clarification; however, the diseses are considered generally to proceed as follows:

When tissues are damaged by bacterial or viaral infection, antibodies are produced against newly formed autoantigens or virally infected cells and the antibodies react with the corresponding antigens to form immune complexes. Since these immune complexes activate the complement system and platelets, vasoactive substances such as histamine and serotonin are released and the permeability of the blood vessels is increased. Then, the immune complexes in circulation enter the vessel wall whose permeabiity has been increased and deposit along the basement membrane. Polymorphonuclear leukocytes gather at the immune complex-deposited site due to the leukocyte chemotactic factors which have been formed by the reaction of the complement to the deposited immune complexes. The polymorphonuclear leukocytes, reacting with the immune complexes, release various tissue-damaging substances such as cathepsins D and E, collagenase, elastase and permeability factors, and these substances eventually damage the tissue. In patients with immune complex diseases such as SLE, levels of the complement in the serum are generally low and aggravation of the disease conditions is closely correlated with the decrease of the complement levels. This decline is thought to be due to plentiful consumption of the complement at the site of the reaction between antigens and antibodies taking place such as in the kidneys and blood vessels. Further, the immune complexes also are related to blood coagulation systems, and it is believed that the immune complexes cause serious symptoms through diverse mechanisms, for example by acceleration of fibrinoid deposition on the damaged tissues.

Currently in use for the treatment of these immune complex diseases are physiotherapy and plasma-replacement therapy in addition to medical treatment with steroids, immunosuppressive agents, anti-inflammatory agents and so forth. In particular, plasma-replacement therapy is one of the most reliable treating methods for removing immune complex, a pathogenic factor, but the advantages of this method are not being sufficiently utilized because of the difficulty in securing the supply of plasma necessary for use in the plasma-replacement.

DESCRIPTION OF THE INVENTION

The present inventors carried out many intensive investigations to develop a treating method which has the same efficacy as plasma-replacement therapy and yet does not require plasma for replacement. As a result, they have found that pepsin and a pepsin-like enzyme contained in leukocytes specifically decompose immune complex at a neutral pH region without affecting normal plasma proteins. On the basis of this finding, they completed an invention relating to a treating agent for immune complex diseases which contains this enzyme as an effective ingredient, see Japanese patent application No. 18429/1981; PCT/JP82/00037. The present invention is an improvement over that previous one, and provides a process for removing immune complex without damaging the inherent functions of plasma proteins. This process comprises treating the plasma from a patient suffering from an immune complex disease with immobilized pepsin. The invention also provides the immobilized pepsin for use in this process.

Since the major objective of plasma-replacement therapy resides in removing nondialyzable pathogenic substances from a patient's plasma, especially immune complex, the treatment of a patient's plasma with the foregoing immobilized pepsin can have the same efficacy as plasma-replacement without the need to replace the plasma. For example, by subjecting plasma from a patient with an immune complex disease to extracorporeal circulation by passing the plasma through a column packed with the above-mentioned immobilized pepsin, only immune complex is removed from the plasma without affecting other plasma proteins. Moreover, since the present process does not require the use of substitute plasma (from the patient or another person), the appearance of side effects such as serum hepatitis or an adverse reaction due to incompatibility of blood can be left out of consideration.

The pepsin used in the present invention is a known enzyme (Journal of Clinical Investigations, Vol. 27, p. 818, 1948); the immobilized pepsin of the present invention can be obtained by purifying pepsinogen contained in the stomach, blood, urine, etc., of various animals by a suitable method, and fixing the purified pepsinogen on a suitable carrier, followed by activating the immobilized pepsinogen in an acid treatment. As the pepsin used for preparation of the immobilized pepsin of the present invention, pepsin derived from humans is preferable because it is the safest and the most effective, but pepsin derived from animals other than humans may also be used. As the carrier to be used for immobilization, carriers having less protein-adsorption capacity such as Sepharose ® (a well-known adsorbent manufactured by Pharmacia Fine Chemicals Co.), agarose, glass beads, etc., are preferable. It is even more preferable to use pepsin immobilized on the inside surface of the filter membrane of an artificial dialyzer, or alternatively, a tube such as a nylon tube is used as a carrier to which pepsin can directly be fixed. Known techniques can be utilized for the immobilization. There can also be employed an immobilized enzyme comprising a pepsin-like enzyme fixed on a suitable carrier, wherein the purified pepsin-like enzyme is obtained by passing a supernatant liquid of homogenized leukocytes of a mammal through a DEAE-cellulose column equilibrated with 0.1M acetate buffer (pH 5.3) to cause the pepsin-like enzyme to be adsorbed on the column, eluting the enzyme with the same buffer containing 0.5M sodium chloride, and subjecting the eluate to gel chromatography on Sephadex G-100 ® (a well-known adsorbent manufactured by Pharmacia Fine Chemicals Co.) swelled in 0.9% physiological saline. This pepsin-like enzyme has the following properties: (a) molecular weight of about 35,000 to 41,000; (b) isoelectric point of pH 2.5 to 3.5; (c) maximum absorption at 278 nm; (d) positive ninhydrin reaction; (e) readily soluble in water and insoluble in ether and chloroform; and (f) white powdery appearance.

For example, according to the method of Seijffers et al (American Journal of Physiology, Vol. 206, p. 1106, 1964), the immobilized enzyme can be prepared by passing human urine through a DEAE-cellulose column equilibrated with 0.1M acetate buffer (pH 5.3) to cause pepsinogen to be adsorbed on the column, then eluting the pepsinogen with the same buffer containing 0.3M sodium chloride, concentrating the eluate, further purifying the concentrate by means of gel chromatography using Sephadex G-100 ® swelled in 0.9% physiological saline, and coupling the purified product to Sepharose ® by the use of cyanogen bromide to obtain immobilized pepsinogen, followed by activating the pepsinogen under acidic conditions.

In carrying out the process of the present invention, it is convenient to utilize what is called extracorporeal circulation, wherein the blood from a patient suffering an immune complex disease is guided to an extracorporeal circuit, and either the whole blood is treated with the foregoing immobilized pepsin, or only the plasma separated from the blood by a plasma separator is treated with the foregoing immobilized pepsin and then recombined with the separated blood cell components, the blood thus treated being returned into the body. The treatment with the immobilized pepsin is preferably carried out either by perfusing the plasma separated by a plasma separator through a column packed with pepsin which has been fixed on Sepharose particles or the like or by perfusing blood or plasma through a hollow tube which carries immobilized pepsin on its inner surface; however, the treatment is not limited to these methods.

For the extracorporeal circulation of blood, it is convenient to use an apparatus composed of a pump for sending out the blood, a plasma separator for the separation of plasma from blood cells, and a controller for the control of these devices. As such an apparatus, there can be utilized the artificial liver-aiding apparatus of a separated plasma perfusion type (Noboru Inoue: Chiryogaku (Therapeutics), Vol. 5, p. 477, 1980). In this method, generally 1-100 mg, preferably 5-50 mg, of the immobilized pepsin is suitably employed for 100 ml of blood, but the amount of the immobilized pepsin can suitably be varied according to the level of the immune complex. The present invention will next be explained in more detail with reference to examples.

BEST MODE FOR CARRYING OUT THE INVENTION

EXAMPLE 1

Distilled water was added to 150 ml of Sepharose 4B ® (a well-known adsorbent manufactured by Pharmacia Fine Chemicals Co.) up to 300 ml of the mixture, and the resulting mixture as adjusted to pH 11.0 with 6N sodium hydroxide solution. To the mixture was then added 300 ml of 2.5% cyanogen bromide, and the pH of the mixture was maintained between 11.0 and 11.5 for 30 minutes while the temperature was maintained at 16° C. The Sepharose ® was washed with distilled water and with 0.1M sodium bicarbonate solution, both of which had previously been cooled to 5° C. to remove the cyanogen bromide. The Sepharose ® was then suspended in 300 ml of the same solution. To 300 ml of the suspension was added 100 mg of human urinary pepsinogen, and the mixture was reacted with gentle stirring at 5° C. for 16 hours to prepare immobilized pepsinogen. The immobilized pepsinogen was then activated at pH 2.0 for 10 minutes to be converted into immobilized pepsin (pepsin 1 mg/ml resin), 100 ml of which was packed into a glass column (4×8 cm).

Heparinized plasma (100 ml) from patients with rheumatoid arthritis and patients with systemic lupus erythematosus who had been proved to carry immune complex in their blood was passed through the immobilized pepsin-column previously warmed to a temperature of 37° C. at the rate of 30 ml per hour. Taking human IgG aggregates as a standard substance, the amounts of immune complex in the plasma before and after the treatment were determined by a hemolytic reaction of sheep erythrocytes using guinea pig complements according to the method of Fust et al (Atherosclerosis, Vol. 29, p. 181, 1978); on the other hand, the amounts of albumin and γ-globulin in the plasma before and after the treatment were determined by electrophoresis using a cellulose acetate membrane (Ikagaku-jikken Koza (Lectures on Experiments in Medical Chemistry), Vol. 5, p. 201, 1973). Tables 1 and 2 show the results, respectively.

After passing the plasma through the immobilized pepsin column, the level of immune complex in the plasma decreased in the case of both diseases, whereas the normal plasma proteins underwent no changes.

TABLE 1

| Disease | No. of plasma | Immune complex level (μg/ml) Before treatment | After treatment |
| --- | --- | --- | --- |
| Rheumatoid arthritis | 1 | 184 | 63 |
|  | 2 | 125 | below 50 |
|  | 3 | 134 | below 50 |
| Systemic lupus erythematosus | 1 | 403 | 123 |
|  | 2 | 253 | 71 |
|  | 3 | 196 | below 50 |

TABLE 2

| Disease | No. of plasma | Albumin (g/dl) Before treatment | After treatment | γ-Globulin (g/dl) Before treatment | After treatment |
| --- | --- | --- | --- | --- | --- |
| Rheumatoid arthritis | 1 | 4.3 | 4.3 | 0.8 | 0.8 |
|  | 2 | 4.9 | 4.9 | 1.0 | 1.0 |
|  | 3 | 5.0 | 5.0 | 1.2 | 1.2 |
| Systemic lupus erythematosus | 1 | 4.8 | 4.8 | 1.3 | 1.3 |
|  | 2 | 5.0 | 5.0 | 1.3 | 1.3 |
|  | 3 | 5.1 | 5.1 | 1.2 | 1.2 |

EXAMPLE 2

In 10 ml of water was suspended 500 mg of aminopropylated glass beads, and the suspension was adjusted to pH 10 with an aqueous solution of 5N sodium hydroxide. To the suspension was added 15 ml of tetrahydrofuran solution containing 1.5 g of cyanogen bromide, and the mixture was kept at pH 10 over a period of 10 minutes while adding an aqueous solution of 5N sodium hydroxide at suitable intervals. The glass beads were collected by filtration and washed with 0.1M sodium bicarbonate solution. The glass beads thus treated were suspended in a mixed solvent of 25 ml of 0.1M aqueous solution of sodium bicarbonate and 25 ml of methanol, which mixed solvent contained 3 moles of methyl 11-aminoundecanoate hydrochloride, and the suspension was reacted at 4° C. overnight, while the pH was kept at 9. The glass beads were collected by filtration, washed with water and methanol, and suspended in 20 ml of absolute methanol. To the suspension was added 1 ml of hydrazine hydrate, and the mixture was stirred for 3 hours. The glass beads were washed with methanol, 0.1N hydrochloric acid, and water, in that order. Then, the beads were suspended in 20 ml of 1N hydrochloric acid. To the suspension was added 280 mg of sodium nitrite, and the mixture was reacted with stirring at 0° C. for 20 minutes.

After the completion of the reaction, the glass beads, washed with a small amount of water, were suspended in 20 ml of 0.1M aqueous solution of sodium bicarbonate (pH 8). Swine pepsinogen (50 mg) was added and dissolved into the suspension, and the mixture was reacted with stirring at 4° C. overnight. The immobilized pepsinogen thus obtained was activated at pH 2 by warming for 10 minutes to convert it into immobilized pepsin, which was suspended in 10 ml of 0.15M physiological saline and packed into a glass column (1×8 cm). Heparinized plasma (10 ml) containing immune complex (from patients suffering from rheumatoid arthritis and systemic lupus erythematosis, respectively) was passed through the foregoing column at the rate of 3 ml per hour. The immune complex level in the plasma and characteristics of other plasma proteins before and after the treatment were examined in the same manner as in Example 1. Tables 3 and 4 show the results, respectively.

After passing the plasma through the immobilized pepsin column, the immune complex level in the plasma decreased in the case of both diseases, whereas the normal plasma proteins underwent no changes.

TABLE 3

| Disease | No. of plasma | Immune complex level (μg/ml) | |
|---|---|---|---|
| | | Before treatment | After treatment |
| Rheumatoid arthritis | 1 | 193 | 58 |
| | 2 | 167 | 65 |
| | 3 | 143 | below 50 |
| Systemic lupus erythematosis | 1 | 353 | 134 |
| | 2 | 296 | 88 |
| | 3 | 199 | below 50 |

TABLE 4

| Disease | No. of plasma | Albumin (g/dl) | | γ-Globulin (g/dl) | |
|---|---|---|---|---|---|
| | | Before treatment | After treatment | Before treatment | After treatment |
| Rheumatoid arthritis | 1 | 4.8 | 4.8 | 0.9 | 0.9 |
| | 2 | 4.7 | 4.7 | 1.0 | 1.0 |
| | 3 | 5.0 | 5.0 | 1.0 | 1.0 |
| Systemic lupus erythematosus | 1 | 4.8 | 4.8 | 1.2 | 1.2 |
| | 2 | 5.1 | 5.1 | 1.2 | 1.2 |
| | 3 | 5.0 | 5.0 | 1.2 | 1.2 |

EXAMPLE 3

A nylon tube of 15 cm in length (inside diameter: 3 mm) was immersed in a water bath controlled at 35° C. Then the inside space of the tube was filled with 4.5N hydrochloric acid, and the tube was subjected to reaction for 15 minutes. The inside of the tube was washed with distilled water and with 0.2M sodium bicarbonate solution (pH 9.4). The inside space of the tube was then filled with 5% glutaraldehyde solution dissolved in the foregoing solution, and the tube was subjected to reaction for 20 minutes. The inside surface of the tube was then washed sufficiently with 0.05M phosphate buffer (pH 8.0), and 5 mg of rat uropepsinogen dissolved in the phosphate buffer was circulated through the tube for reaction at the rate of 0.2 ml/min for 2 hours so as to fix the pepsinogen on the inside surface of the tube. The inside surface of the tube was then activated by treating with hydrochloric acid solution of pH 2 for 10 minutes to convert the pepsinogen into immobilized pepsin.

According to the method of Suzuki et al (Folia Pharmacologica Japonica, Vol. 68, p. 572 (1972)), anti-rat kidney rabbit serum was injected intravenously at a dose of 5 ml/kg into Wistar strain male rats in groups each consisting of 6 rats to induce nephritis. Twenty-one days after inducing the nephritis, 2 injection needles that had been treated with heparin were inserted and fixed in the jugular vein of each rat to form an extracorporeal circuit by connecting the 2 injection needles with the foregoing tube, and the circulation was carried out at the rate of 2 ml per hour for 4 hours. As a control, a tube having no immobilized pepsin was used in the same manner. The immune complex levels in the blood after the extracorporeal circulation were determined in the same manner as in Example 1. Table 5 shows the results.

By the circulation of blood through the tube having an inside surface upon which was fixed immobilized pepsin, the immune complex level in the blood decreased remarkably.

TABLE 5

| | Immune complex level (μg/ml) |
|---|---|
| Control group | 283 ± 29 |
| Immobilized pepsin group | 195 ± 11* |

*$p < 0.05$

EXAMPLE 4

A plasma separator of a filtration type with hollow threads of cellulose acetate was fitted into the cubital vein of each of 5 adult dogs anesthetized with pentobarbital (body weight: 10–15 kg). The immobilized pepsin column prepared in Example 1 was connected to a heparinzed perfusion circuit for plasma, and the plasma was introduced to the circuit at a controlled flow rate of 30 ml per hour by means of a flow rate adjustable pump (Perista pump Ato). The plasma which had passed through the immobilized pepsin column and the blood cell components which had been separated were combined together, and returned into the body through an extracorporeal circulation circuit formed with the cubital vein on the other side. 40 mg/kg of soluble immune complex (prepared at a ratio of human IgG: anti-human IgG rabbit antibody=4:1) was injected intravenously into the femoral vein by means of a continuous infusion syringe (Truth A-II type) over a period of 3 hours. As a control, a Sepharose ® column free of immobilized pepsin was used in the same manner. Three hours after the extracorporeal circulation had been started, the immune complex level in the plasma was determined in the same manner as in Example 1. Table 6 shows the results.

After passing the plasma through the immobilized pepsin column, the immune complex level in the plasma decreased remarkably.

TABLE 6

|  | Immune complex level (μg/ml) |
| --- | --- |
| Control group | 343 ± 27 |
| Immobilized pepsin group | 105 ± 11** |

**p < 0.01

EXAMPLE 5

100 mg of human gastric pepsinogen was fixed on the inside surface of a filter membrane of a hollow fiber type artificial dialyzer (Dow-4 Cordis) with the use of cyanogen bromide and then activated with hydrochloric acid of pH 2.0 for 10 minutes to be converted into immobilized pepsin. Two hundred milliliters (5 cases) of heparinized blood containing immune complex was circulated through the artificial dialyzer at the rate of 10 ml per minute. As a control, an artificial dialyzer having no immobilized pepsin was used in the same manner. After 2 hours of circulation, the plasma was separated, and the immune complex level was determined according to the method of Example 1. Table 7 shows the results.

After circulation of the blood through the immobilized pepsin, the immune complex level in the blood decreased remarkably.

TABLE 7

|  | Immune complex level (μg/ml) |
| --- | --- |
| Control group | 203 ± 19 |
| Immobilized pepsin group | 128 ± 17* |

*p < 0.05

As described in the foregoing examples, the immobilized pepsin of the present invention decreases the amount of an immune complex in blood without affecting in any way normal plasma proteins. Therefore, immune complex in the blood of a patient with an immune complex disease can be removed without damage to physiological functions of the blood by treating the blood or the plasma of the patient with the immobilized pepsin, followed by returning the treated blood or plasma through perfusion to the patient's body. This fact is extremely significant because it means that the utilization of the immobilized pepsin and the process for removing immune complex can produce the same result as is obtained by plasma replacement therapy, without a need for plasma for replacement.

What is claimed is:

1. A process for removing immune complexes from blood or plasma, comprising contacting blood or plasma containing immune complexes with a material comprising an effective agent immobilized on a pharmaceutically acceptable carrier, said agent being selected from the group consisting of pepsin and an enzyme derived from mammalian leukocytes, and recovering said blood or plasma freed of said immune complexes, said enzyme having the following properties:
    (a) molecular weight of about 35,000 to 41,000;
    (b) isoelectric point of pH 2.5 to 3.5;
    (c) maximum absorption at 278 nm;
    (d) positive ninhydrin reaction;
    (e) readily soluble in water and insoluble in ether and chloroform; and
    (f) white powdery appearance.

2. A process according to claim 1, wherein said agent is pepsin derived from human urine.

3. A process according to claim 1, wherein said agent is pepsin derived from a non-human animal.

4. A process according to claim 1, wherein said carrier is selected from the group consisting of Sepharose, agarose and glass beads, and said material is packed into a column before being contacted with said blood or plasma.

5. A process according to claim 2, wherein said carrier is selected from the group consisting of Sepharose, agarose and glass beads, and said material is packed into a column before being contacted with said blood or plasma.

6. A process according to claim 1, wherein said carrier includes a filter membrane of an artificial dialyzer.

7. A process according to claim 2, wherein said carrier includes a filter membrane of an artificial dialyzer.

8. A process according to claim 1, wherein said carrier includes an inside surface of a tube.

9. A process according to claim 2, wherein said carrier includes an inside surface of a tube.

10. A method for treating a patient suffering from an immune complex disease, comprising contacting blood or plasma of said patient with a material comprising an effective agent immobilized on a pharmaceutically effective carrier, said agent being selected from the group consisting of pepsin and an enzyme derived from mammalian leukocytes, recovering said blood or plasma freed of said immune complexes, and returning said blood or plasma to said patient, said enzyme having the following properties:
    (a) molecular weight of about 35,000 to 41,000;
    (b) isoelectric point of pH 2.5 to 3.5;
    (c) maximum absorption at 278 nm;
    (d) positive ninhydrin reaction;
    (e) readily soluble in water and insoluble in ether and chloroform; and
    (f) white powdery appearance.

11. A method according to claim 10, wherein said disease is selected from the group consisting of rheumatoid arthritis, systemic lupus erythematosis and lupus nephritis.

12. A method according to claim 10, wherein said blood or plasma is contacted with said material in an extracorporeal circuit.

13. A method according to claim 10, wherein whole untreated blood is contacted with said material.

14. A method according to claim 12, wherein said extracorporeal circuit includes an artificial dialyzer, and said carrier includes a filter membrane of said artificial dialyzer.

15. A method according to claim 10, wherein said carrier is selected from the group consisting of Sepharose, agarose and glass beads.

16. A method according to claim 10, wherein said carrier includes an inside surface of a tube.

17. A method according to claim 10, wherein 1–100 mg of said material is contacted with each 100 ml of blood or plasma.

18. A method according to claim 10, wherein 5–50 mg of said material is contacted with 100 ml of said blood or plasma.

19. A method according to claim 10, wherein said blood or plasma is contacted with said material at a rate of 3–30 ml/hr.

20. A method according to claim 10, wherein said agent is pepsin derived from human urine.

* * * * *